United States Patent [19]
Fletcher et al.

[11] B 3,984,681
[45] Oct. 5, 1976

[54] ION AND ELECTRON DETECTOR FOR USE IN AN ICR SPECTROMETER

[76] Inventors: James C. Fletcher, Administrator of the National Aeronautics and Space Administration, with respect to an invention of; Wesley T. Huntress, Sierra Madre, Calif.

[22] Filed: Aug. 27, 1974

[21] Appl. No.: 500,981

[44] Published under the second Trial Voluntary Protest Program on January 27, 1976 as document No. B 500,981.

[52] U.S. Cl. .............................. 250/291; 250/290
[51] Int. Cl.² ........................................ H01J 39/46
[58] Field of Search ............ 250/290, 291, 292, 293

[56] References Cited
UNITED STATES PATENTS

| | | | |
|---|---|---|---|
| 3,475,605 | 10/1969 | Llewellyn | 250/290 |
| 3,484,602 | 12/1965 | McIlraith | 250/290 |
| 3,511,986 | 5/1970 | Llewellyn | 250/292 |

*Primary Examiner*—James W. Lawrence
*Assistant Examiner*—B. C. Anderson
*Attorney, Agent, or Firm*—Monte F. Mott; Paul F. McCaul; John R. Manning

[57] ABSTRACT

A detector for detecting ions and/or electrons present in a resonance cell of an ICR spectrometer is disclosed. The detector which operates on the Q-meter principle is driven by an external rf oscillator capable of providing rf frequencies up to about 15MHz at an adjustable low rf signal level, e.g., below 20mV. The detector is connected across the resonance of the cell to detect ions by detecting their cyclotron frequency. Electrons are detectable by connecting the detector across the cell's trapping plates and thereby detect the electrons' trapping motion, the frequency of which is in the megahertz range.

18 Claims, 7 Drawing Figures

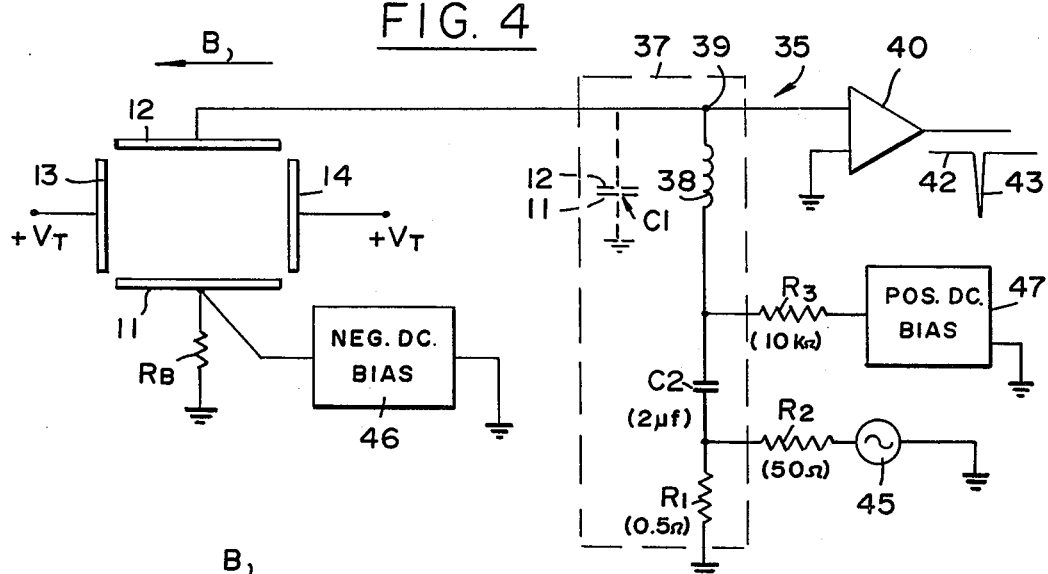
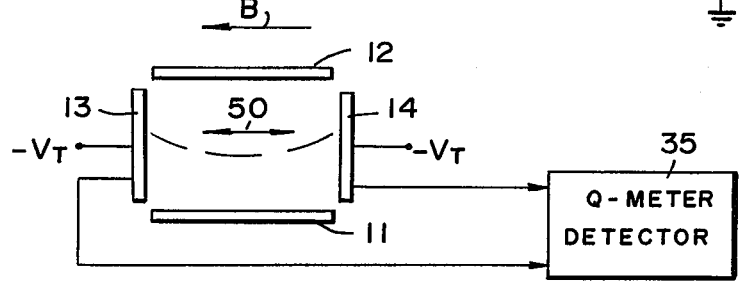
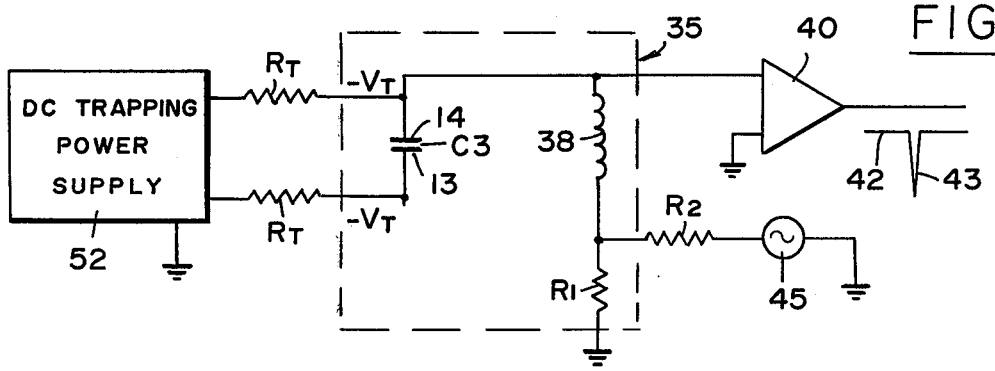
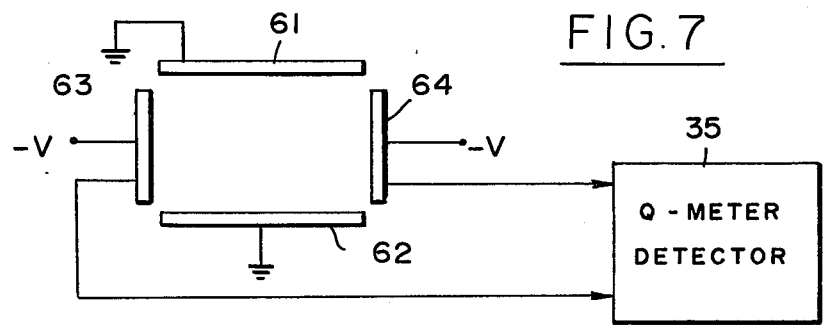

ION AND ELECTRON DETECTOR FOR USE IN AN ICR SPECTROMETER

ORIGIN OF INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

BACKGROUND OF THE INVENTION

1. Field of the Invention:

The present invention generally relates to the field of ion cyclotron resonance (ICR) spectroscopy and, more particularly, to a new ion and electron detector for use in an ICR spectrometer.

2. Description of the Prior Art:

In an ICR spectrometer the analyzer cell which is also referred to as the resonance cell is typically rectangular in shape and consists of four plates. These include a base plate which is parallel to and spaced apart along a first axis from a top plate and two parallel side plates which are spaced apart from each other along a second axis, which is orthogonal to the first axis. The base and top plates are often referred to as the drift or resonance plates and the two side plates as the trapping plates. A magnetic field is applied in the direction of the second axis, i.e., in the direction along which the trapping plates are spaced apart. A dc potential is applied to each of the trapping plates with respect to the base plate in order to establish a potential thereacross, whose function is to center any ions in the cell about the cell center. The types of ions present in the cell are detected by a detector which is connected across the resonance plates.

The detector which is most extensively used in the prior art is of the marginal oscillator type. Basically, it consists of a tuned circuit in which the resonance plates define a capacitive element of simply a capacitor. The marginal oscillator detector is tuned to a fixed frequency in the radio frequency (rf) range, and uses a feedback resistor to provide oscillation at a constant rf amplitude.

The magnetic field causes the ions in the cell to undergo a cyclotron motion or oscillation in a plane perpendicular to the magnetic field. The frequency of the cyclotron motion, hereinafter also referred to as the cyclotron frequency oscillation, is dependent on the mass of the ions in the cell and the magnetic field. When the ion's cyclotron frequency equals that of the detector's fixed frequency, the Q of the detector's tuned circuit drops sharply, which causes a sharp drop in the detector's output. The mass of the ions present in the cell is identified from the rf frequency and the amplitude of the magnetic field when such drops occurs. Such cells and the marginal oscillator detector are extensively described in the literature and in U.S. Patents including U.S. Pat. Nos. 3,446,957, 3,475,605, 3,505,516, and 3,511,986. See for example, U.S. Pat. No. 3,475,605, column 2, line 66 in which the oscillator detector is referred to as the marginal oscillator.

There are several significant disadvantages in the prior art arrangements. The cyclotron frequency of low mass ions with $M/e = 1-10$, except at very weak magnetic fields below about 3,000 gauss (G), is on the order of several megahertz (MHz). At frequencies of several MHz the rf level of the marginal oscillator detector is too high for most ICR experiments. A high rf level excites ion cyclotron motion of large amplitude, causing many ions to strike the resonance plates and thereby become neutralized. This causes undesired loss of ions from the cell. It is for this reason that the rf frequency provided in the prior art by the marginal oscillator detector is limited to be below about 1MHz and thereby limit the rf level to be sufficiently low for the ICR experiments. The desired rf level is on the order of 20mV and less for most experiments. Since the cyclotron frequency of low mass ions, except at weak magnetic fields, is generally above 1MHz, these ions cannot be detected easily with the marginal oscillator detector at typical magnetic fields between 3,000 and 12,000 G. For the foregoing reasons, the marginal oscillator detector is not very useful for the detector of ions in the ICR spectrometer where the cyclotron frequencies are on the order of several Megahertz, e.g., 2–15MHz. The marginal oscillator detector cannot produce such rf frequencies at sufficiently low rf levels.

In addition to the above limitations the marginal oscillator detector is completely useless to detect electrons, whose cyclotron frequency is in the Gigahertz range. Thus, a need exists for a new type detector for use with an ICR resonance cell to detect ions at high cyclotron frequencies, e.g., 2–15MHz and a need exists for an arrangement to detect the presence of electrons in an ICR cell.

OBJECTS AND SUMMARY OF THE INVENTION

It is a primary object of the present invention to provide a new type of detector for use with an ICR cell to detect ions and electrons.

Another object of the present invention is to provide a new detector ICR cell arrangement for detecting ions or electrons in the cell.

A further object of the invention is to provide a new type detector capable of providing rf frequencies up to about 15MHz at relatively low levels, for use in combination with an ICR cell to detect ions or electrons therein.

These and other objects of the invention are achieved by providing a detector comprising a tuned resonant circuit driven by an external rf oscillator. The rf oscillator is one which is capable of providing rf frequencies in the MHz range, e.g., up to 15MHz, at a relatively low rf level, which is independent of the rf frequency and is adjustable. The detector in essence operates on the same principle as a Q-meter, and therefore hereinafter may be referred to as the Q-meter detector. In this detector the rf frequency of the oscillator is adjustable to be sufficiently high enough to detect low mass ions when a high magnetic field is applied. Yet the rf level of the oscillator is adjustable to be sufficiently low to prevent excessive cyclotron excitation of the ions, thus preventing their striking the resonance plates.

To detect ions the Q-meter detector is connected across resonance plates of the cell, in the same way that such a cell is connected in the prior art to the marginal oscillator detector.

The Q-meter detector can also be used to detect electrons present in the ICR cell. In accordance with the present invention to detect electrons, the Q-meter detector is connected across the trapping plates of the cell, rather than across the resonance plates. In this arrangement, the frequency of the trapping motion of the electrons, which is in the form of a simple harmonic motion between the trapping plates and which is on the order of several MHz, is utilized to determine the presence of electrons.

The novel features of the invention are set forth with particularity in the appended claims. The invention will best be understood from the following description when read in conjunction with the accompanying drawings.

BRIEF DESCRIPTION OF THE DRAWINGS

FIG. 4 is an end view of the ICR cell and the schematic diagram of the novel Q-meter detector of the present invention;

FIG. 5 is an end view of the ICR cell and its connection to the Q-meter detector to detect electrons in the cell;

FIG. 6 is a schematic diagram of the arrangement shown in FIG. 5; and

FIG. 7 is a diagram of an arrangement for detecting electrons in a quadrupolar field.

DESCRIPTION OF THE PREFERRED EMBODIMENTS

Figure 1:
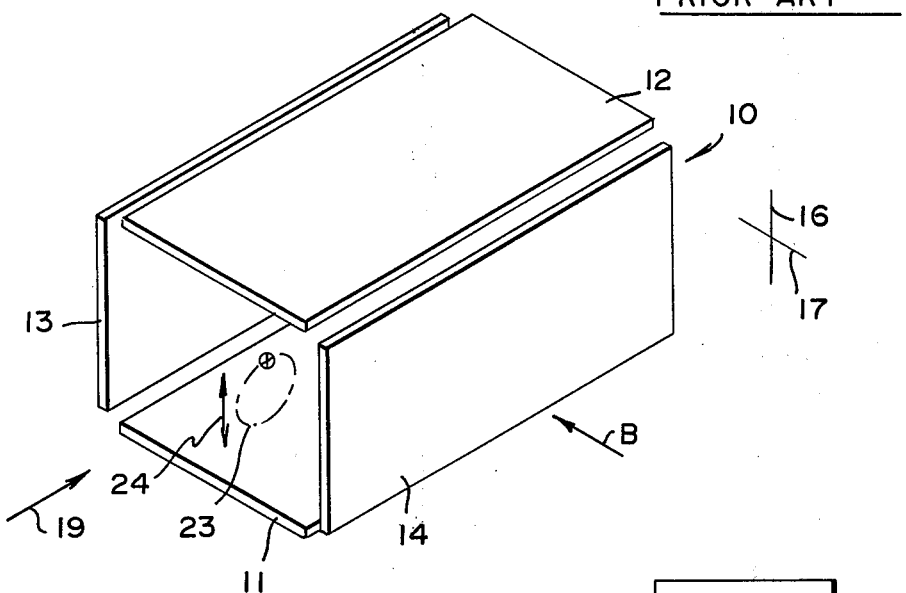
FIG. 1 is an isometric view of an ICR cell.
Figure 2:
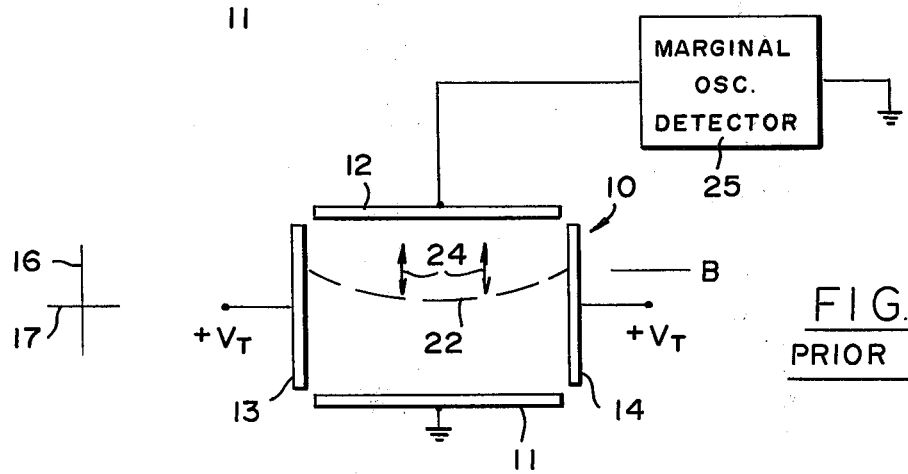
FIG. 2 is an end view of the cell and a prior art marginal oscillator detector, shown in block form.
Figure 3:
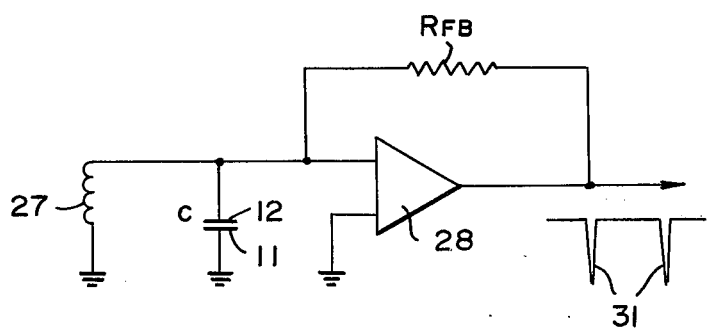
FIG. 3 is a simple schematic diagram of the prior art marginal oscillator detector.

The present invention may best be explained by first briefly describing in connection with FIGS. 1–3 the prior art typical ICR cell, and the marginal oscillator detector used therewith. The typical ICR cell 10 (FIGS. 1 and 2) consists of four spaced apart plates. These include a bottom plate 11, which is parallel to a top plate 12, and two parallel side plates 13 and 14. Plates 11 and 12 which are the resonance plates are spaced apart along a first axis 16 and the side 13 and 14 are spaced apart along a second axis 17, which is perpendicular to axis 16. Plates 13 and 14 represent the trapping plates. FIG. 2 is a view of the plates in the direction of arrow 19.

The resonance plates are generally dc biased so that at the cell center between them, the dc potential is zero or ground. In many ICR applications a small dc bias has to be applied to plate 12 with respect to plate 11 so as to cause ions present in the cell to drift down the length of the cell in the direction of arrow 19. This may be achieved by applying a small negative dc bias to plate 11 from a power supply (not shown) with a very low impedance to ground at the operating rf frequency and a positive dc bias to plate 11. For explanatory purposes, however, the dc biasing of plates 11 and 12 is deleted from FIGS. 2 and 3, and plate 11 is shown as grounded at the operating rf frequencies.

Typically, each of the plates 13 and 14 is connected to a dc potential with respect to ground to establish a trapping well potential in the cell which is designated in FIG. 2 by dashed line 22. The dc potential is often referred to as the dc bias trapping voltage. It is positive for the detection of positive ions and negative for negative ions. In FIG. 1, it is designated by $+V_T$. A magnetic field B, generally of a variable amplitude, is applied in the direction of axis 17. Due to the magnetic field B, any ions present in the cell 10 undergo cyclotron oscillation in a plane which is perpendicular to the magnetic field, as represented by numeral 23 in FIG. 1 and arrows 24 in FIG. 2.

The function of the dc bias trapping voltage is to establish the trapping well potential and thereby center the oscillating ions about the cell center. The ion trapping time (or duration) in the cell is directly related to the magnetic field amplitude. In many experiments a magnetic field of several thousand gauss (G), e.g., 3,000 G and more is required to insure a sufficiently long trapping duration.

The detection of ions in the cell is achieved by connecting a detector 25 to the top plate 12. In the prior art the detector 25 is a marginal oscillator detector shown schematically in FIG. 3. It includes a tuned circuit comprising an inductor 27 connected across the top and bottom plates 12 and 11, which electrically define a capacitor C. The detector 25 also includes an amplifier 28 and a feedback resistor $R_{FB}$. Ion detection is achieved by sweeping (varying) the magnetic field B at a fixed oscillator frequency $\omega_{rf}$. When the ion cyclotron frequency, designated $\omega_c$, equals $\omega_{rf}$, an effective resistance appears across capacitor C, thereby lowering the Q of the tank circuit which results in a sharp reduction in the amplitude, or output, of the amplifier 28. These reductions are represented in FIG. 3 by spikes 31. Knowing $\omega_{rf}$ and the amplitude of the magnetic field B when the spikes 31 occur, the type of ions, i.e., the charge over mass ratio of the ions is determined based on the known relationship of $\omega_{rf} = \omega_c = (q/m) B$.

The major disadvantages of such an arrangement is that at higher rf frequencies, the rf amplitude of the marginal oscillator is generally higher than at low rf frequencies. A high rf signal level excites ion cyclotron motion along axis 16. Thus, if the signal level is too high the excited ion cyclotron motion often results in ions striking the top or bottom resonance plate, 11 or 12, and thereby becoming neutralized. To prevent this phenomenon from occurring, low rf signal levels generally below 20mV, are desired in ICR experiments. Such low rf levels can be attained with a marginal oscillator detector only if its rf frequency is on the order of less than 1MHz. However, operation at low frequencies is undesirable for several reasons: 1) the mass resolution and sensitivity are poorest at low rf frequencies, 2) in ion trapping experiments, low mass ions are more efficiently trapped at high magnetic fields, which requires high frequencies, i.e., for fields on the order of several thousand G the cyclotron frequencies for $M/e = 1 - 10$ are on the order of several MHz, e.g., up to 15MHz. Thus, the marginal oscillator detector is of very limited use in these situations.

All of the these disadvantages are eliminated by utilizing the novel Q-meter detector of the present invention, designated by numeral 35 in FIG. 4 and which is schematically diagrammed therein together with the cell 10. It includes a tuned circuit 37 which effectively consists of an inductor or coil 38 connected at one end 39 to an amplifier 40 and to the top plate 12 of the cell 10. Plate 12 together with grounded plate 11 represent the capacitive element C1 of the tuned circuit. C1 is shown in FIG. 4 in dashed lines since in reality it is formed by plates 11 and 12. The output of amplifier 40 is represented by waveform 42 with spikes 43.

The rf frequency is injected into the tuned circuit 37 from an external rf oscillator 45 through a resistance divider consisting of a very small resistor R1 and a resistor R2. In one embodiment R1 is about 0.5 ohm ($\Omega$) and R2 is 50$\Omega$. The rf oscillator 45 is one which is capable of providing the desired rf frequency, e.g., up to 15MHz, at an rf level which is independent of the frequency. Thus, rf signals at the desired high frequency may be injected into the cell yet at a sufficiently low level to prevent excessive ion cyclotron motion excitation. One example of oscillator 45 is HP model 606A. As previously indicated for some ICR applications a small dc bias has to be applied to plate 12 with respect to plate 11, in order to force ions which are present in the cell to drift down the cell in the direction of arrow 19 (see FIG. 1) which is in a direction perpendicular to both axes 16 and 17. This may be achieved by applying a small negative dc bias to plate 11 and a small positive dc bias to plate 12. Plate 11 is shown connected to ground through a relatively large resistor $R_B$ to ground and to negative dc bias power supply 46. The latter exhibits a very low impedance to ground at the rf frequencies. Thus, from an rf point of view, plate 11 is practically grounded.

The small positive dc bias for plate 12 is provided by a positive dc bias power supply 47. The power supply 47 is connected to the tuned circuit through a relatively large, e.g., 10kΩ resistor R3, which effectively isolates the rf voltage in the tuned circuit from the low impedance dc power supply.

The dc bias provided by power supply 47 is isolated from the rf oscillator 45 output by incorporating a relatively large, e.g., 2μf capacitor C2. Its reactance at frequencies above 1MHz is practically negligible. Thus, at the operating frequencies, the tuned circuit 37 effectively consists of the small (0.5Ω) resistor R1 connected in series with coil 38, across which the cell's plates 11 and 12, representing the capacitive element C1 are connected. If desired, the power supply 47 may be connected through $R_3$ to the top plate 12 and capacitor C2 placed between plate 12 and coil 38.

It was discovered that there is only a negligible loss in Q of the tuned circuit due to the presence of the small series resistance of R1. Such loss in Q is less than that experienced when the rf is injected through a large resistor in series with a tuned circuit consisting of only inductor 38 connected in parallel across plates 11 and 12. The reasons for this is that a large resistor on the order of 10μΩ has in general a small parallel capacitive reactance on the order of 1μF. At frequencies on the order of 1MHz and above this would result in a low impedance shunt to ground across the cell of approximately 200kΩ and a large loss in Q of the tuned circuit.

Using the Q meter detector of the present invention, and when the cyclotron frequency equals the rf frequency provided by oscillator 47, power absorption by the ions present in the cell 10 appears as a resistive load across the capacitive element in the tuned circuit 37, i.e., across plates 11 and 12 which define C1. This lowers the effective Q of the tuned circuit 37, resulting in spike 43 in the output of amplifier 40. This mode of operation is practically identical with that of the prior art marginal oscillator detector. However, in the Q-meter detector of the present invention the rf frequency provided by oscillator 45 can be adjusted independent of the rf level. Thus, the rf frequency can be made as high as required for the experiment yet a sufficiently low rf level can be attained to prevent excessive ion cyclotron motion excitation. Therefore, the Q meter detector can be used with great advantage together with the ICR cell to detect all ions even at large rf frequencies.

To detect all ions even in the presence of high magnetic fields above about 3,000G, the desired upper frequency limit of oscillator 45 should be about 15MHz. The lower frequency limit should be as low as the lowest ion cyclotron frequency expected in any experiment. The rf level should be adjustable to be sufficiently low, e.g., 20mV and less at any rf frequency within the operating range. For the best performance (signal to noise ratio), the Q of the resonant circuit should be as high as possible. For this reason, the rf insertion resistor R1 should be very small, with minimum inductive reactance. Also, strong capacity in the tuned circuit should be kept to a minimum and the coil should have a very high Q factor. To cover the frequency range of up to 15MHz, the tank circuit may include several high quality coils, only one of which is chosen for any experiment depending on the particular rf frequency which is employed.

While the Q meter detector of the present invention is particularly useful to identify ions by detecting their cyclotron frequencies (up to about 15MHz), it cannot be used to identify electrons by detecting their cyclotron frequencies. As is appreciated any electrons present in cell 10 also undergo cyclotron resonance oscillation. However, the cyclotron frequencies of electrons even at low magnetic fields are very high, generally in the Gigahertz range. For example, the cyclotron frequency of electrons at 1000G is about 2.8GHz, which is much too high for detection in a practical experiment.

However, electrons, in addition to undergoing cyclotron oscillation in the Gigahertz frequency range, also under a simple harmonic motion in the trapping well in the direction of axis 17, as represented by arrow 50 in FIG. 5, which is a diagram of the Q-meter detector 35 and cell 10. The frequency of this motion for an electron, hereinafter referred to as the electron trapping frequency is in the MHz range for a cell in which the spacings between the trapping plates is on the order of one inch and the dc bias trapping voltage $V_T$ is on the order of 1 volt. The general expression for the electron trapping frequency, designated $f_e$ is $$f_e = \frac{5.3}{d} \sqrt{V_T \text{ MHz}},$$

where $d$ is the distance between the trapping plates 13 and 14, as well as the distance between the resonance plates 11 and 12. That is, the cell as viewed along arrow 19 is square-shaped. When $d = 1$ inch and $V_T = 1$ volt $$f_e = \frac{5.3}{1} \sqrt{1} = 5.3 \text{MHz}.$$

The magnitude in megahertz of $f_e$ differs slightly from the above expression when the cell in the direction of arrow 19 is rectangular rather than square-shaped. In either case it is in the range of several megahertz.

In accordance with the present invention the presence of electrons in the cell 10 is detected by connecting the Q-meter detector 35 across the trapping plates 13 and 14 as shown in FIG. 5 rather than across the resonance plates 11 and 12. As shown in FIG. 6 which is a schematic diagram of the Q-meter detector for electron detection, the trapping plates 13 and 14 represented by C3 are connected across the coil 38. To detect electrons, each of plates 13 and 14 are at a negative bias trapping voltage designated $-V_T$ below ground. The $-V_T$ voltage is applied to each plate through a separate resistor $R_T$ from a dc bias trapping power supply 52.

To detect the presence of electrons in the cell the rf frequency of oscillator 45 is adjusted to equal $f_e$ based on the distance d of the particular cell and the dc bias trapping voltage $V_T$. For a cell with $d=1$ inch, and $V_T=1$ volt, the rf frequency of oscillator 45 is adjusted to be 5.3MHz. The presence of any electrons is indicated by a spike in the detector's output.

From the foregoing, it is thus seen that in accordance with the present invention, a Q-meter ICR cell arrangement is provided to enable the detection of electrons in the cell. This basic arrangement can be extended to detect simultaneously both electrons and negative ions. The electrons can be detected by one Q-meter detector connected to the trapping plates 13 and 14 to detect the electron trapping frequency as shown in FIG. 6 and the negative ions can be detected by another Q-meter detector connected across plates 11 and 12 as shown in FIG. 4 to detect the ions' cyclotron frequency. Also, the detection of electrons in accordance with the present invention is not limited to those present in an ICR cell. The Q-meter detector can be used to detect the presence of electrons moving in a quadrupolar electric field. The electrons need not be collected at an electrode, but rather are detected by resonance absorption at their frequency of harmonic motion in one plate of the quadrupolar field which is analogous to the trapping frequency in the ICR cell. The magnetic field is not essential for detection of electrons in the quadrupolar field.

The quadrupolar field may be established by four spaced apart plates or rods such as plates 61–64 shown in FIG. 7. Two opposite plates such as 61 and 62 may be grounded and the other two plates 63 and 64 connected to a positive or negative dc source. The Q-meter detector can be connected to eitherpair of plates. The rf frequency of oscillator 45 is adjusted to equal $f_e$ in accordance with the above expression. In such an arrangement any electrons present in the field will cause the detector's output to produce a spike as previously explained.

It should be pointed out that the same basic arrangement can be used to detect ions, present in the quadrupolar field. However, for such detection the Q-meter detector should be operated at a considerably lower frequency since the ion trapping frequency is considerably lower than that of electrons. It is about 20KHz for an ion of mass 40.

Although particular embodiments of the invention have been described and illustrated herein, it is recognized that modifications and variations may readily occur to those skilled in the art and consequently, it is intended that the claims be interpreted to cover such modifications and equivalents.

What is claimed is:

1. A detector for use in an ion cyclotron resonance (ICR) spectrometer of the type including a resonance cell through which ions move, the cell including first and second parallel resonance plates spaced apart along a first axis, and first and second parallel trapping plates, spaced apart along a second axis perpendicular to said first axis, said spectrometer including means for applying a magnetic field in the direction of said second axis, and means for applying a preselected potential between each of said trapping plates and a reference potential, the detector comprising:

a coil;
means connecting said coil substantially across said first and second resonance plates, the latter defining a capacitive element which together with said coil form a tuned circuit;
an external radio frequency (rf) oscillator adapted to provide signals at frequencies up to the megahertz range, at relatively low adjustable (rf) voltage levels which are independent of the signals' frequencies;
injecting means for connecting said oscillator to said tuned circuit to inject signals at a selected level and frequency from said oscillator into said tuned circuit; and
means for sensing the level of the signals across said tuned circuit.

2. The detector as described in claim 1 wherein said coil having a first end which is connected to said second resonance plate and a second end, said injecting means including a first resistor connected between said second coil end and ground and a second resistor connected between said coil second end and said oscillator, means for effectively connecting said second resonance plate to ground at the frequency provided by said oscillator, and said sensing means is connected across said coil first end and ground, to sense the signal level at said coil first end with respect to ground.

3. The detector as described in claim 2 wherein the resistance of said first resistor is less than one ohm.

4. The detector as described in claim 3 wherein the resistance of said second resistor is on the order of fifty ohms.

5. The detector as described in claim 2 wherein said reference potential is ground and said preselected potential applied to each trapping plate with respect to ground is positive when the ions in said cell are positive and is negative when the ions in the cell are negative.

6. The detector as described in claim 5 further including means for dc biasing each of the resonance plates to an opposite polarity with respect to ground, whereby the dc potential at a midpoint between said resonance plates is substantially ground.

7. The detector as described in claim 1 wherein said first resonance plate is substantially grounded at the frequencies provided by said oscillator, said detector includes a capacitor and a first resistor connected together with said coil in series between ground and said second resonance plate, with said coil having a first end connected to said second resonance plate, and said first resistor having one end connected to ground, with said capacitor being connected between a second end of said coil and a second end of said first resistor, said injecting means including a second resistor connected between said oscillator and the junction point of said capacitor and said first resistor, and bias means including a dc power supply connected to the junction point of said coil and said capacitor to apply a dc bias potential to said second resonance plate through said coil, the capacitor being characterized by a negligible reactance at the frequency of the rf signals provided by said oscillator.

8. The detector as described in claim 7 wherein the resistance of said first resistor is less than one ohm.

9. The detector as described in claim 8 wherein the resistance of said second resistor is on the order of fifty ohms.

10. The detector as described in claim 7 further including means for dc biasing each of the resonance plates to an opposite polarity with respect to ground, whereby the dc potential at a midpoint between said resonance plates is substantially ground.

11. A detector for use with a resonance cell in a cyclotron resonance spectrometer to detect the presence of electrons in the cell, the cell including first and second parallel resonance plates, spaced apart along a first axis, and first and second parallel trapping plates, spaced apart along a second axis perpendicular to said first axis, the detector comprising:

means for biasing said resonance plates whereby a midpoint between said resonance plates is at ground potential;

means for applying a negative dc bias potential to each of said trapping plates with respect to ground;

a coil;

means for connecting said first and second trapping plates substantially across said coil to form a tuned circuit therewith, with said trapping plates defining a capacitive element;

an oscillator for providing (rf) signals in the megahertz frequency range at selectable signal levels;

means for connecting said oscillator to said tuned circuit to inject therein said signals at a selected low (rf) voltage level and at a frequency definable as $f_e$, where $f_e$ in megahertz is substantially equal to $(5.3/d)(V_T)^{1/2}$, where $d$ is the spacing between said trapping plates and the spacing between said resonance plates in inches, and $V_T$ is the negative bias potential with respect to ground; and sensing means coupled to said tuned circuit, for sensing the signal level across said circuit, the signal level dropping appreciably when said oscillator provides signals at said frequency $f_e$ and electrons are present in said cell.

12. The detector as described in claim 11 wherein said means for connecting include a first resistor connected between a first end of said coil and ground and a second resistor connected between said coil first end and said oscillator.

13. The detector as described in claim 12 wherein the resistance of said first resistor is less than one ohm.

14. The detector as described in claim 13 wherein the resistance of said second resistor is on the order of fifty ohms.

15. An arrangement for detecting the presence of charged particles in a quadrupolar field, the arrangement comprising:

first means for establishing a quadrupolar field including first and second elements, which are at a first negative dc potential with respect to a reference dc potential definable as ground, and which are spaced apart along a firxt axis, and third and fourth elements which are at a second dc potential with respect to ground and which are spaced apart along a second axis perpendicular to said first axis;

a coil;

means for connecting either said first and second elements or said third and fourth elements substantially across said coil to form a tuned circuit therewith;

an oscillator for providing (rf) frequency signals at frequencies up to the megahertz range at selectable signal levels;

means for connecting said oscillator to said tuned circuit to inject therein said signals at a selected frequency and low (rf) voltage level, the selected frequency being a function of the type of charged particles to be detected, and the spacings of said first and second elements along said first axis, and the third and fourth elements along said second axis; and sensing means coupled to said tuned circuit for detecting the signal level across said circuit.

16. The arrangement as described in claim 15 wherein said first element is effectively at ground potential at the selected frequency, and wherein said second element is connected to a first end of said coil, said coil having a second end, said injecting means including a first resistor connected between the coil second end and ground and a second resistor connected between said oscillator and said coil second end, whereby at the selected frequency said first and second elements are connected across said coil and said first resistor, between ground and the coil first end, and said sensing means being coupled between ground and the coil first end.

17. The arrangement as described in claim 16 wherein the selected frequency is in the megahertz range when said charged particles are electrons.

18. The arrangement as described in claim 16 wherein the resistances of said first and second resistor are respectively in the range of 1 and 50 ohms.

* * * * *